United States Patent [19]

Holden

[11] 4,330,748
[45] May 18, 1982

[54] FREQUENCY CORRECTION CIRCUITRY FOR PIPELINE SENSOR APPARATUS

[75] Inventor: Ernest M. Holden, Newcastle, England

[73] Assignee: British Gas Corporation, London, England

[21] Appl. No.: 33,013

[22] Filed: Apr. 24, 1979

[30] Foreign Application Priority Data

Mar. 16, 1979 [GB] United Kingdom ............. 799436

[51] Int. Cl.³ .................. G01R 33/00; G01N 27/72; G01N 27/82
[52] U.S. Cl. .................................. 324/225; 324/220
[58] Field of Search ............ 324/219, 220, 221, 225, 324/240

[56] References Cited

U.S. PATENT DOCUMENTS

| | | | |
|---|---|---|---|
| 2,881,386 | 4/1959 | Price et al. ........................ | 324/225 |
| 3,714,558 | 1/1973 | Swanepoel ........................ | 324/225 |
| 3,786,684 | 1/1974 | Wiers et al. ....................... | 324/220 |

OTHER PUBLICATIONS

"Handbook of Operational Amplifier Active RC Networks", Burr-Brown Research Corp., 1966, pp. 74–75.

*Primary Examiner*—Gerard R. Strecker
*Assistant Examiner*—Walter E. Snow
*Attorney, Agent, or Firm*—Watson, Cole, Grindle & Watson

[57] ABSTRACT

In one method of non-destructive inspection of bodies of ferromagnetic material such as buried or submerged pipelines, probes containing magnetic sensors scan the surface of the body to detect flaws as local variations in the magnetic field. Such sensors are sensitive to changes in velocity of the probe carrier which manifests itself in variations of output signal amplitude. Such variations are eliminated by matching the sensor with a correction circuit having complementary frequency response characteristics.

This technique may be used in conjunction with a threshold circuit to eliminate unwanted data.

3 Claims, 6 Drawing Figures

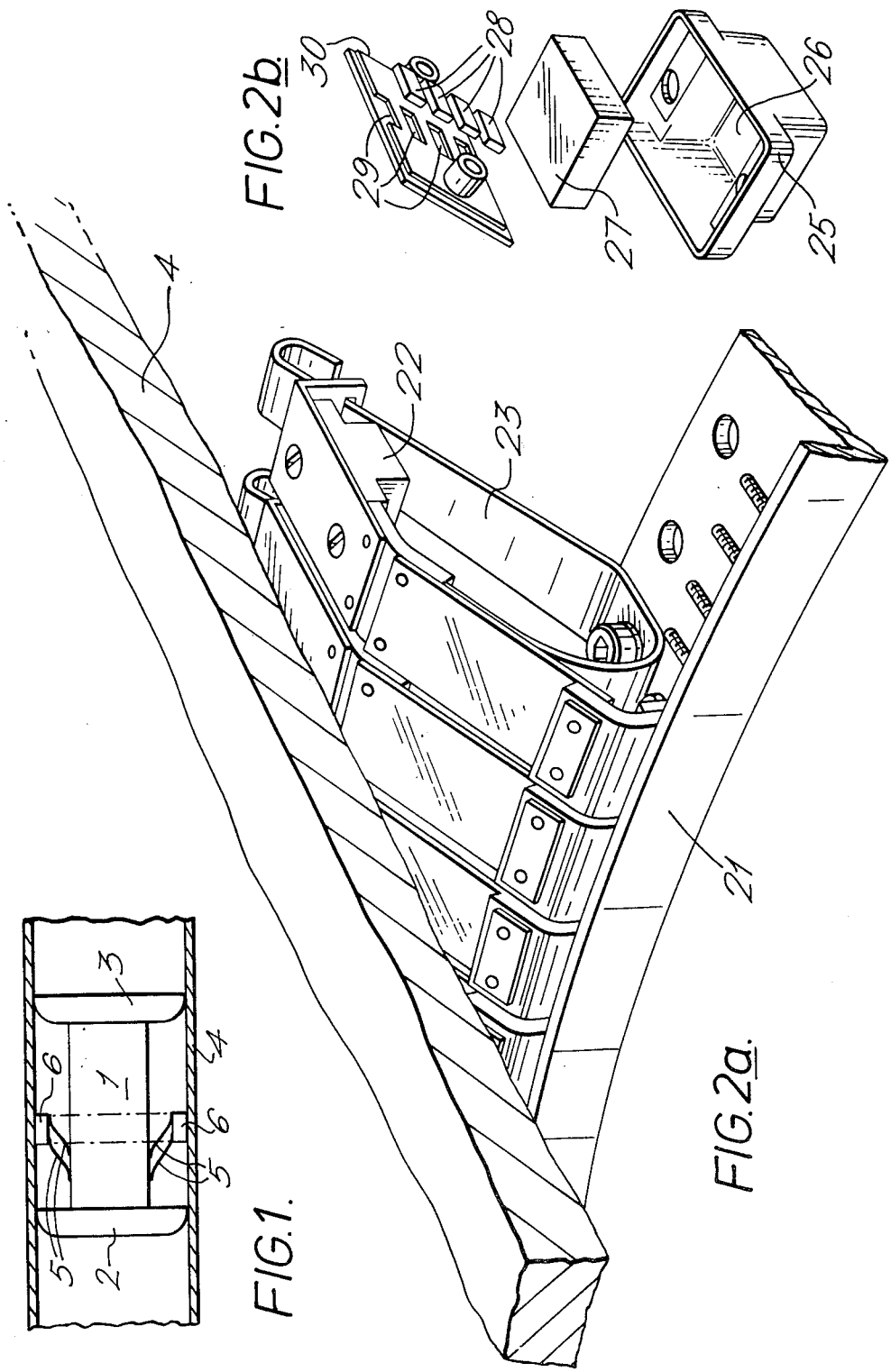

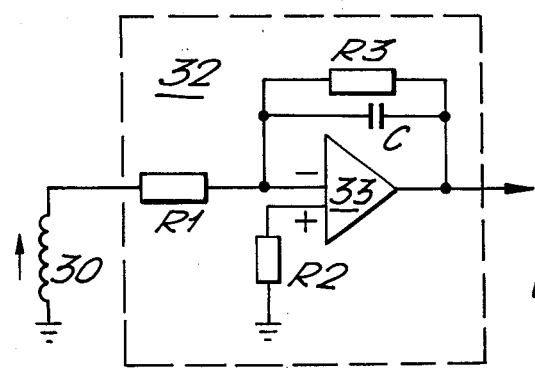
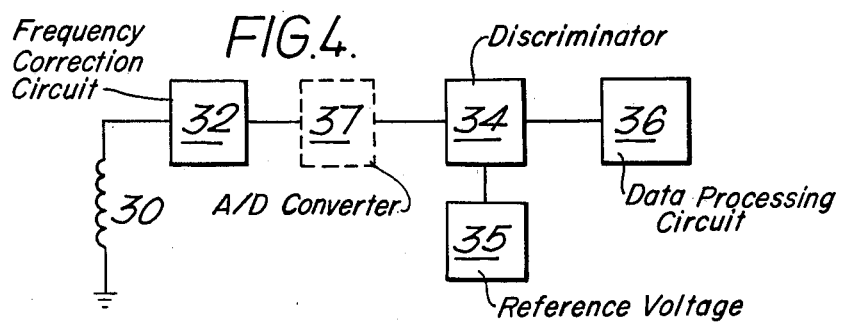
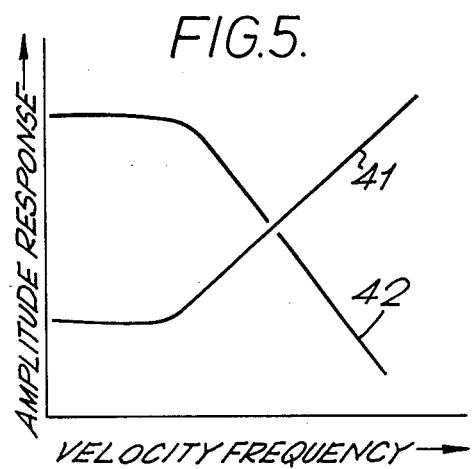

FREQUENCY CORRECTION CIRCUITRY FOR PIPELINE SENSOR APPARATUS

BACKGROUND

1. Field of the Invention

This invention relates to the non-destructive testing of ferromagnetic materials and, in particular, to means for reducing the sensitivity of test apparatus to variations in relative velocity of an object under test and a probe head supplying the test apparatus.

Many devices for the non-destructive testing of ferromagnetic materials rely on inductive sensors such as pickup coils to detect local differences in magnetic field and produce an electrical signal dependent thereon. These signals may be recorded, fed on to some form of data processing apparatus or simply displayed on an indicator device. However, the differences in magnetic field which they represent are, in turn, indicative of local variations in the object under test. These variations may result from flaws or profile irregularities or inhomogeneities in the materials of which the object is constructed. The voltage induced in an inductive pickup coil is given by $$V = k(d\phi/dt)$$

where $d\phi/dt$ is the rate of change of magnetic field and k is a constant which depends on the geometry and magnetic properties of the pickup coil.

A major application of methods of non-destructive testing of ferromagnetic materials is the inspection of pipelines which are buried below the ground or submerged in water and are used to transport gases and liquids. Inspection vehicles known as pigs may be driven by fluid pressure and traverse the pipeline with the fluid. These inspection pigs carry test apparatus which includes sensors to investigate properties of the pipeline. They may carry recording equipment or use telemetry to transmit the test measurements to a remote location. A typical method and apparatus for the non-destructive testing of ferromagnetic pipelines is described in our co-pending British application No. 3189/77.

2. Prior Art

When carrying out measurements on test objects, it is frequently convenient to preprocess the data before transmitting it to a remote location or recording it. This may be necessary because the facility for recording or transmitting the data has only a limited bandwidth or dynamic range, or it may be simply to filter out unwanted data for ease of evaluation and interpretation. One such system is the use of a trigger threshold as is described in DAS No. 2,704,132, where the method is employed for statistical sampling of an ultrasonic signal. Another system is to filter the transducer signals so that only those characteristic of the parameters of interest are allowed to pass; this method is followed in instruments for investigating the surface profiles produced by machining. Yet another system is to perform an auto-correlation process on signals produced by a measuring transducer; one form of seismological surveying uses this technique.

SUMMARY OF THE INVENTION

Test probes for monitoring properties of pipelines may feed a threshold device so that only those features of interest are detected. However, as previously indicated, the amplitude of the output signal from an inductive probe is dependent on the rate of change of magnetic flux in the vicinity of the probe head. This in turn, will be proportional to the relative velocity of the probe head with respect to the object under test. In order, therefore, to include some form of amplitude discrimination in the probe signal processing circuit it is useful to include a frequency correction circuit so that the overall signal level is not sensitive to changes in velocity. For a normal inductive pickup coil, a linear roll-off characteristic will suffice, but, in general, a circuit must be selected to have a transfer characteristic which is the inverse of the velocity sensitivity of the probe head sensor. Such a frequency correction circuit has the additional advantage of reducing the overall dynamic range of signals to be processed.

Accordingly, the present invention provides apparatus for nondestructive testing of a body of ferromagnetic material comprising a probe containing an electromagnetic sensor to produce an electrical signal in response to variations in the magnetic field in the vicinity of the sensor, means to move said probe relative to an object under test and frequency correcting circuit means connected to the sensor to compensate for variations in output signal amplitude caused by variations in the velocity of the probe with respect to the object.

Preferably the apparatus also includes threshold means connected to the frequency correcting circuit means to give a first output signal when the input signal from the frequency correcting circuit means is at or above a predetermined threshold level and a second output signal when the output signal is below the threshold level. The use of such a frequency correcting circuit allows a fixed threshold reference even though the velocity of the probe sensor may vary.

An embodiment of the invention will now be described by way of example with reference to the accompanying drawings in which:

FIG. 1 shows schematically a pipeline inspection pig having shoes to carry inductive probe heads FIG. 2a shows a practical arrangement of a pickup carrier shoe, FIG. 2b shows the arrangement of components within the shoe of FIG. 2a, FIG. 3 is a schematic diagram of a frequency correcting circuit for an inductive probe head, FIG. 4 is a block diagram showing schematically an arrangement of apparatus for non-destructive testing of pipelines, and FIG. 5 shows the pickup response curve and a complementary frequency correcting transfer characteristic.

DETAILED DESCRIPTION OF A PREFERRED EMBODIMENT

Referring now to the drawings, an inspection pig 1 has scraper cups 2, 3 which form a seal with the wall of a pipeline 4 to position the pig and to drive it through the pipeline by pressure differences generated across the pig by the fluid medium transported through the pipeline. Mounted on leaf springs 5 are shoes 6 in which inductive pickup coils are held.

In the practical embodiment shown in FIGS. 2a and 2b, the sensor shoe is mounted by means of leaf springs 23 on a flanged ring 21 attached to the pig (not shown). The shoe carries an enclosure member 25 having a hollow in which a permanent magnet 27 is placed. Inductive pickup coils 28 are mounted in recesses 29 in the lid 30 of the enclosure member.

Signals from a pickup coil 30 (FIG. 3) are fed to a frequency correction circuit 32. This consists of input resistor R1 and an amplifier 33 to which is connected a feedback circuit consisting of a resistor R3 and a capacitor C in parallel. Such a circuit exhibits a roll-off of 6 dB/ octave at frequencies above a turnover frequency set by the time constant of the feedback circuit. Referring to FIG. 4, the output of the frequency correction circuit 32 is connected to a discriminator 34 which gives an output to a data processing circuit 36 when the input signal is above a predetermined amplitude threshold and no output when the input signal is below this level. The threshold level may be an analogue value derived from a reference voltage with a comparator being used as a discriminator, or alternatively, an analogue/ digital converter 37 may be inserted in the signal path and the comparison performed digitally.

FIG. 5 shows the variation 41 of the pickup output with velocity and the complementary transfer characteristic 42 of the frequency correcting circuit to which the pickup is connected.

Although a pickup having a linear characteristic has been described, the invention envisages pickups with other characteristics. In such cases, a signal transfer circuit having a complementary characteristic will be chosen.

Furthermore, although the invention has been described with respect to pipeline inspection pigs, it will be clear to one skilled in the art that the use of complementary transfer and response characteristics to compensate for velocity sensitivity of a pickup sensor is equally applicable to other forms of test apparatus.

I claim:

1. Apparatus for non-destructive testing of an object of ferromagnetic material, comprising:
    a probe movable with respect to the object and including means for generating a magnetic field in the object and an electromagnetic sensor responsive to variations in the magnetic field of the ferromagnetic material in the vicinity of the sensor to generate an electrical signal having an amplitude and frequency varying with the velocity of the probe with respect to the object; and
    frequency correcting circuit means responsive only to said electrical signal and having a transfer characteristics which is the inverse of the velocity sensitivity of the electromagnetic sensor to compensate for variations in the amplitudes of said electrical signal.

2. Apparatus as claimed in claim 1 further comprising threshold means connected to said frequency correcting circuit means to generate a first output signal when the input signal from said frequency correcting circuit means is at or above a predetermined threshold level and a second output signal when the input signal is below said threshold level.

3. Apparatus as claimed in claim 2 wherein the sensitivity of the sensor increases with increasing velocity of the probe with respect to the object and the response of said frequency correcting circuit means falls off with increasing frequency.

* * * * *